United States Patent [19]

Bach et al.

[11] Patent Number: 5,417,882
[45] Date of Patent: May 23, 1995

[54] LIQUID-CRYSTALLINE COMPOUNDS

[75] Inventors: Volker Bach, Neustadt; Karl-Heinz Etzbach; Karl Siemensmeyer, both of Frankenthal; Gerhard Wagenblast, Weisenheim, all of Germany

[73] Assignee: BASF Aktiengesellschaft, Ludwigshafen, Germany

[21] Appl. No.: 849,565

[22] Filed: Mar. 11, 1992

[30] Foreign Application Priority Data

Mar. 16, 1991 [DE] Germany .................. 41 08 627.9

[51] Int. Cl.$^6$ ............... C09K 19/52; C09K 19/12; C07C 255/54; C07C 69/76
[52] U.S. Cl. ....................... 252/299.1; 252/299.61; 252/299.62; 252/299.66; 252/299.67; 560/8; 558/411; 558/414; 544/335
[58] Field of Search ............ 252/299.1, 299.5, 299.6, 252/299.61, 299.69, 299.66, 299.67; 428/1; 544/335; 558/411, 414; 560/8

[56] References Cited

U.S. PATENT DOCUMENTS

| | | | |
|---|---|---|---|
| 4,728,547 | 1/1988 | Vaz et al. | 252/299.66 |
| 4,891,152 | 1/1990 | Miller et al. | 252/299.1 |
| 4,971,719 | 11/1990 | Vaz et al. | 252/299.5 |
| 4,997,591 | 3/1991 | Heppke et al. | 252/299.61 |
| 5,021,188 | 6/1991 | Vaz et al. | 252/299.5 |

FOREIGN PATENT DOCUMENTS

| | | |
|---|---|---|
| 2188048 | 9/1987 | United Kingdom . |
| 2210381 | 6/1989 | United Kingdom . |
| 91/16295 | 10/1991 | WIPO . |

OTHER PUBLICATIONS

Eidenschink et al., *Liquid Crystals*, vol. 8, No. 6, pp. 879–884, Jul. 5, 1990.
Velver & Hatz, "Handbook of Liquid Crystals", Verlag Chemie, 1980 69–113.

*Primary Examiner*—Shean Wu
*Attorney, Agent, or Firm*—Keil & Weinkauf

[57] ABSTRACT

Liquid-crystalline compounds of the formulae I and II, $$Z^1-(X^1-R^1-Y-M)_m \qquad \text{I}$$

$$Z^2-(X^2-R^1-Y-M)_n \qquad \text{II}$$

where
$Z^1$ is the radical of an m-valent alcohol an m-valent acid or certain trivalent triazine derivatives; $Z^2$ is an n-valent radical of a monocyclic or polycyclic aromatic compound; $X^1$ is a chemical bond or —CO—; $X^2$ is —O—, —S—, —CO—O—, —O—CO—, —SO$_2$—, —SO$_2$—O—, —O—SO$_2$—O—, —NR$^4$—, —CO—NR$^4$—NR$^4$—O— or —CO—N<, where R$^4$ is H or C$_1$-C$_8$-alkyl; m and n are 3 to 6; R$^1$ is a C$_2$-C$_{20}$-bridge having 2 to 12 bridging members, which may be interrupted by —O—, —S— or —NR$^4$—, each of these hetero units being separated by at least 2 carbon atoms; Y is a chemical bond, —O—, —S—, —CO—O—, —O—CO—, —NR$^4$—, —CO—NR$^4$— or —NR$^4$—CO—; M is a mesogenic group. These compounds are suitable for the production of optical and electro-optical data carriers and display elements.

4 Claims, No Drawings

LIQUID-CRYSTALLINE COMPOUNDS

BACKGROUND OF THE INVENTION

1. Field of the Invention

The present invention relates to liquid-crystal-line compounds of the formulae I and II $$Z^1-(X^1-R^1-Y-M)_m \qquad \text{I}$$

$$Z^2-(X^2-R^1-Y-M)_n \qquad \text{II}$$

where $Z^1$ is the alcoholate or acid radical $Z^1/1$ of an m-valent aliphatic alcohol or of an m-valent aliphatic carboxylic acid having 3 to 30 carbon atoms; the alcoholate or acid radical $Z^1/2$ of an m-valent cycloaliphatic alcohol or of an m-valent cycloaliphatic carboxylic acid having 5 or 6 ring members, in the case where m=3, the nitrogen-containing radical $Z^1/3$ $$N \begin{cases} (CH_2-CH_2-O-)_p \\ (CH_2-CH_2-O-)_p \\ (CH_2-CH_2-O-)_p \end{cases}$$

where p may be 1 or 2, in the case where m=3, a radical having the structure $Z^1/4a$–d

[structures a, b, c, d shown]

a: triazine with -O- substituents and =O
b: triazine with -S- substituents and =S
c: triazine with -HN-, -NH-, NH substituents
d: cyclic structure with -O-CH$_2$-CH$_2$-N- and CH$_2$-CH$_2$-O- groups in the case where m=3 or m=4, the acid radical $Z^1/5$ of nitrilotriacetic acid or of ethylenediaminetetraacetic acid, the radical $Z^1/6$ $$\begin{bmatrix} CO- \\ | \\ NH- \end{bmatrix} \begin{bmatrix} CO- \\ | \\ (CH_2)_q N- \end{bmatrix}_{m-1} -H$$

where q may be 2 or 3,
$Z^2$ is the n-valent radical $Z^2/1$ of a benzene

[benzene ring with $(R^2)_r$ substituents]

where $R^2$ may be halogen, cyano, nitro, $C_1$–$C_{10}$-alkyl, $C_1$- to $C_{10}$-alkoxy, $C_1$- to $C_{10}$-alkoxycarbonyl, $C_1$- to $C_{10}$-acyloxy or radicals which are bonded to the ring in the vicinal position, r is zero to 3, and the radicals $R^2$, in the case where r>1, may be identical or different, the polycyclic radical $Z^2/2$

[structure showing three phenyl rings with $R^3$ substituents linked by $CH_2$ groups, with subscript n-2]

where $R^3$ may be $C_1$- to $C_4$-alkyl, $C_1$- to $C_4$-alkoxy or halogen, in the case where n=3, the phosphorus-containing radical $Z^2/3$ $$(O)_sP \begin{cases} Ph- \\ Ph- \\ Ph- \end{cases}$$

where s may be zero or 1;

$X^1$ is a chemical bond or —CO—,
$X^2$ is oxygen, sulfur, —CO—O—, —O—CO—, —SO$_2$—, —SO$_2$—O—, —O—SO$_2$—O—, NR$^4$—, —CO—NR$^4$—, —NR$^4$—O— or —CO—N<, where R$^4$ may be hydrogen or $C_1$- to $C_8$- alkyl, with the proviso that, in the case of the polycyclic radical $Z^2/2$, $X^2$ can only be —O— or —O—CO—,
m is 3 to 6, with the proviso that m is less than or equal to the number of carbon atoms in $Z^1$,
n is 3 to 6,
$R^1$ is a $C_2$- to $C_{20}$-bridge containing 2 to 12 bridging members, which may be interrupted by oxygen, sulfur or —NR$^4$—, it being possible for each of these hetero units to be separated by at least 2 carbon atoms,
Y is a chemical bond, oxygen, sulfur, —CO—O—, —O—CO—, —NR$^4$—, —CO—NR$^4$— or —NR$^4$—CO—, and
M is a mesogenic group derived from a compound which, in the liquid-crystalline phase, has an anisotropy of the dielectric constant $\epsilon$ where $|\Delta\epsilon|>0.3$ and/or which is optically active.

The invention also relates to processes for the preparation of the compounds I and II, and to the use thereof in the form of solid or liquid-crystalline, optically anisotropic media for the display and storage of information.

2. Description of the Prior Art

Liquid-crystalline compounds are optically anisotropic substances which, in contrast to liquids, have a long-range order of the molecules, it being possible for the molecules to have a regular one- or two-dimensional arrangement and to form liquid-crystalline mesophases. With respect to the spatial arrangement of the molecular units within the liquid crystal, a distinction is made between essentially 3 phases:

the nematic phase, the cholesteric phase and the smectic phase.

In nematic phases, the individual molecules are aligned in one direction. Their structural feature is a parallel alignment of the molecular long axes at the same time as a random distribution of the molecular centers of gravity. The molecules have no lateral cohesion; there is therefore no layer structure as in the smectic phases described below. The molecules can move relative to one another along their long axes, ie. they can slip past one another freely, which causes their low viscosity. Nematic phases therefore have much lower viscosity than smectic phases.

The structure of the cholesteric phase, which can only be achieved with optically active molecules, is closely related to that of the nematic phase. It is therefore frequently also known as the chiral nematic phase. As in the nematic phase, the molecular long axes of the liquid-crystalline compounds are aligned parallel to one another, but the preferential direction of the molecular long axes changes regularly from layer to layer through a certain angle. Within an individual layer, a uniform preferential direction exists which is twisted in the same direction through a constant angle with respect to the preferential direction within the adjacent layer. A helical arrangement of the molecular long axes thus forms over a plurality of layers. The helical structure is caused by the chirality of the participating molecules.

Smectic phases have a two-dimensional structure. Intermolecular interactions cause the elongate, rod-like molecules aligned parallel to one another to form layers, which are stacked at identical separations from one another. Various modifications can occur here, differing in the arrangement of the molecules within the layers. Smectic phases $S_A$ to $S_I$ are known. For example, the centers of gravity of the molecules can be arranged randomly ($S_A$ and $S_C$ phases) or regularly ($S_B$ phase) within a layer. The molecular long axes can be parallel or tilted to the perpendiculars on a layer plane. The molecules cannot leave the layer plane since virtually no interactive forces exist between the ends of the molecules. Although this allows the layers to move slightly relative to one another, the more highly ordered state (two-dimensional structure) means that the viscosity of smectic phases is greater than for nematic phases.

Furthermore, smectic liquid-crystalline phases are known which have an electrical spontaneous polarization in the absence of an external electrical field. This polarization can be reoriented by applying an external electrical field; these phases are hence known as ferroelectric smectic liquid-crystalline phases. A typical example is the chiral $S_c$ phase ($S_c^*$ phase). Due to their anisotropic optical and dielectric properties, they can be utilized for electro-optical display elements (abbreviated to displays). Thus, ferroelectric displays based on $S_c^*$ phases allow extremely rapid writing and deletion of symbols.

The following symbols characterize liquid-crystalline phases or liquid-crystalline behavior:

S denotes a smectic liquid-crystalline phase or smectic liquid-crystalline behavior, N denotes a nematic liquid-crystalline phase or nematic liquid-crystalline behavior, N* denotes a cholesteric (chiral nematic) liquid-crystalline phase or cholesteric (chiral nematic) liquid-crystalline behavior, where means that the liquid-crystalline compound contains a chiral, ie. optically active, center and it is therefore possible for optically active liquid-crystalline phases to form.

When a solid liquid-crystalline compound melts, a smectic phase, for example, is formed first as a liquid-crystalline phase; as the temperature is increased further, this is converted either into a further liquid-crystalline phase, for example a nematic phase, or, at the clearing point, into the optically isotropic melt, at phase-transition temperatures which are characteristic of each compound. When the melt is cooled, the liquid-crystalline phases and finally the crystalline liquid crystal re-format the corresponding transition temperatures. This interconversion of the liquid-crystalline compound is known as enantiotropic conversion.

Some liquid crystals are compounds in which it is possible to freeze the liquid-crystalline phase once formed. To this end, the liquid-crystalline melt is cooled below a certain temperature, so that an optically anisotropic solid is formed which is not crystalline, but glassy.

Liquid-crystalline compounds which solidify to form glass-like materials are found both amongst low-molecular-weight organic compounds and amongst polymeric organic compounds. In known polymeric liquid crystals, polyacrylic and polymethacrylic chains, inter alia, serve as the main polymer chains. Structural units of low-molecular-weight liquid-crystalline compounds as side groups are linked to this polymer backbone via polymeranalogous reactions.

EP-B 90 282 discloses polymers based on esters and amides of acrylic acid and methacrylic acid which form liquid-crystalline phases. The side chains linked to the main polymer chain via the ester and amide functions comprise a flexible, long-chain moiety which maintains the separation (also known as a spacer) and a mesogenic group or pleochroic dye and effect the formation of liquid-crystalline phases.

Suitable spacers are alkylene groups having 2 to 12 carbon atoms which may be linear or branched and may be interrupted by oxygen, sulfur and/or $R^6$—N< groups where $R^6$ is hydrogen or substituted or unsubstituted alkyl.

Examples of mesogenic groups are those mentioned, for example, in Kelker and Hatz, Handbook of Liquid Crystals, Verlag Chemie 1980, pages 69 to 113.

Depending on the spacers and/or mesogenic groups, the polymers may form liquid-crystalline phases and can be employed alone or together with low-molecular-weight liquid crystals in electro-optical displays.

In principle, the electro-optical displays comprise a 6 to 30 μm liquid-crystalline layer between two glass plates, each of which is coated on the inside with an electrode layer and at least one of which must be transparent. The transparent, electroconductive top layers used are in particular antimony-doped tin oxide layers and tin oxide-doped indium oxide layers.

DE-A 39 17 196 discloses monomers of the formula V

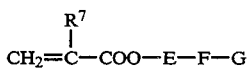

V where $R^7$ is hydrogen, chlorine or methyl, E is a flexible spacer, F is a mesogenic moiety which is built up from at least three aromatic rings linked in a linear or approximately linear manner and which contains at least one 2,6-naphthalene group, and G is an optically active chiral moiety. These monomers are used to prepare polymers containing chiral mesogenic side groups with a ferroelectric smectic liquid-crystalline behavior.

A disadvantage of using polymeric liquid crystals is the slow speed of the switching processes. A further disadvantage is that polymeric liquid crystals, unlike low-molecular-weight compounds, cannot be synthesized in a uniform, defined molecular weight.

Known low-molecular-weight liquid crystals include liquid-crystalline compounds having glass phases, which can be used in industry and electro-optics due to their characteristic phase properties.

DE-A 37 03 640 describes glass-like, liquid-crystalline, 2-substituted 1,4-bis(4-substituted benzoyloxy)benzenes. They are employed alone, in mixtures with one another or with other liquid-crystalline or non-liquid-crystalline substances as anisotropic, solid, optical media for the production of optical components and for thermoelectro-optical storage displays at room temperature.

Corresponding areas of application exist for the 1,4-bis(2,3,4-substituted benzoyloxy)benzenes disclosed in DE-A 38 30 968, which form nematic phases which solidify to form glass-like materials.

DE-A 38 27 603 discloses chiral, smectic liquid-crystalline compounds of the formula VI $$M_1{}^*—K—M_2{}^* \qquad \text{VI}$$

where $M_1{}^*$ and $M_2{}^*$ are identical chiral, smectogenic groups, and —K— is a divalent group. They have the property of simultaneously solidifying from the liquid-crystalline phase on cooling to give glass-like materials.

The low-molecular-weight liquid-crystalline compounds having glass phases known hitherto have the common property that their glass phases do not have long-term stability and therefore take on a crystalline ordered state after a brief time at room temperature. The information previously written is lost due to this crystallization process. A further disadvantage is their low anisotropy of the dielectric constant $\Delta\epsilon$, which is crucial for the alignment of the molecules in the electrical field. The dielectric anisotropy is the difference between the dielectric constants $\epsilon$ measured parallel and perpendicular to the resultant preferential direction given from the alignment of all the molecular long axes. The values for the dielectric constant $\epsilon$ measured parallel to the preferential direction are denoted by $\epsilon\|$ and the values measured perpendicular thereto are denoted by $\epsilon_\perp$. The dielectric anisotropy ($\Delta\epsilon = \epsilon\| - \epsilon_\perp$) may be positive or negative. If $\epsilon\|$ is greater than $\epsilon_\perp$ and $\Delta\epsilon$ is thus positive, the liquid crystal aligns itself with its optical axis parallel to the field. If $\Delta\epsilon$ is negative, the optical axis aligns itself perpendicular to the field.

SUMMARY OF THE INVENTION

It is an object of the present invention to provide liquid-crystalline compounds which have high dielectric anisotropy, are homogeneous substances having a defined molecular weight and low viscosity and, in pure form, can be switched reproducibly and rapidly at the low temperatures occurring in practice, and which can store information written by the switching process.

We have found that this object is achieved by the liquid-crystalline compounds I and II defined at the outset.

We have furthermore found various processes, described below in greater detail, for the preparation of the liquid-crystalline compounds I and II, and that these compounds can be used alone, in mixtures with one another and with other liquid-crystalline and/or non-liquid-crystalline compounds in the form of solid or liquid-crystalline, optically anisotropic media for the display and storage of information.

DESCRIPTION OF THE PREFERRED EMBODIMENTS

The liquid-crystalline compounds described by the formulae I and II $$Z^1—(X^1—R^1—Y—M)_m \qquad \text{I}$$

$$Z^2—(X^2—R^1—Y—M)_n \qquad \text{II}$$

are based on central units denoted by $Z^1$ and $Z^2$. $X^1$ is a chemical bond or —CO—, and $X^2$ is, very generally, a hetero unit which, like $X^1$, is bonded to a $C_2$- to $C_{20}$-bridge which is described by $R^1$ and is known as a spacer. Y is in turn a chemical bond or a hetero unit, and M is a mesogenic group derived from a compound which, in the liquid-crystalline phase, has an anisotropy of the dielectric constant $\epsilon$ where $|\Delta\epsilon|$ is $>0.3$ and/or which is optically active.

m is a number from 3 to 6, with the proviso that m is less than or equal to the number of carbon atoms in $Z^1$; n is a number from 3 to 6.

The central unit $Z^1$ is a radical derived, for example, from the following compounds: from aliphatic alcohols, such as
  glycerol,
  1,2,4-butanetriol,
  2-methyl-2-hydroxymethyl-1,3-propanediol,
  2-ethyl-2-hydroxymethyl-1,3-propanediol,
  1,2,3,4-butanetetraol,
  pentaerythritol,
  xylitol,
  mannitol and
  sorbitol,
from aliphatic carboxylic acids, such as
  1,2,3-propanetricarboxylic acid,
  1,1,4-butanetricarboxylic acid,
  1,2,3,4-butanetetracarboxylic acid, citric acid and
  2-hydroxynonadecyl-1,2,3-tricarboxylic acid,
from cycloaliphatic alcohols having 5 or 6 ring members, such as
  1,2,3,4-tetrahydroxycyclopentane,
  1,2,3-trihydroxycyclohexane,
  1,2,4-trihydroxycyclohexane,
  1,3,5-trihydroxycyclohexane,
  1,2,3,4-tetrahydroxycyclohexane,
  1,2,3,5-tetrahydroxycyclohexane,
  1,2,4,5-tetrahydroxycyclohexane,
  1,2,3,4,5-pentahydroxycyclohexane and
  1,2,3,4,5,6-hexahydroxycyclohexane,
from cycloaliphatic carboxylic acids having 5 or 6 ring members, such as
  1,2,3-cyclopentanetricarboxylic acid,
  1,2,4-cyclopentanetricarboxylic acid,
  2-methyl-1,2,3-cyclopentanetricarboxylic acid,
  3-methyl-1,2,4-cyclopentanetricarboxylic acid,
  1,1,2,2-cyclopentanetetracarboxylic acid,
  1,2,2,4-cyclopentanetetracarboxylic acid,
  1,1,3,3-cyclopentanetetracarboxylic acid,
  1,2,3,4-cyclopentanetetracarboxylic acid, 1,2,3,4,5-cyclopentanepentacarboxylic acid,
1,1,4-cyclohexanetricarboxylic acid,
1,2,4-cyclohexanetricarboxylic acid,
1,3,5-cyclohexanetricarboxylic acid,
1,1,3,3-cyclohexanetetracarboxylic acid,
1,1,4,4-cyclohexanetetracarboxylic acid,
1,2,3,4-cyclohexanetetracarboxylic acid,
1,2,4,5-cyclohexanetetracarboxylic acid,
1,1,3,3,5-cyclohexanepentacarboxylic acid and
1,2,3,4,5,6-cyclohexanehexacarboxylic acid,
from alkoholamines, such as
triethanolamine,
triisopropanolamine and
aminoethylethanolamine,
from triazine derivatives, such as
cyanuric acid,
thiocyanuric acid,
melamine and
trishydroxyethyl isocyanurate,
from nitrilotriacetic acid and ethylenediaminotetraacetic acid, and from the radical

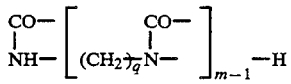

where q may be 2 or 3.

Particularly suitable central units $Z^1$ are glycerol, pentaerythritol, mannitol and citric acid.

The central unit $Z^2$ is an n-valent radical $Z^2/1$ of a benzene

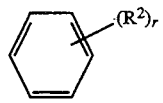

where $R^2$ may be halogen, cyano, nitro, $C_1$- to $C_{10}$- alkyl, $C_1$- to $C_{10}$- alkoxy, $C_1$- to $C_{10}$- alkoxycarbonyl, $C_1$- to $C_{10}$- acyloxy or radicals bonded to a ring in the vicinal position, r is zero to 3, and $R^2$, in the case where r is $>1$, may be identical or different.

For example, the central unit $Z^2$ is a radical $Z^2/1$ derived from a compound such as
1,2,3-trihydroxybenzene,
1,2,4-trihydroxybenzene,
1,3,5-trihydroxybenzene,
1,2,3,4-tetrahydroxybenzene,
1,2,3,5-tetrahydroxybenzene,
1,2,4,5-tetrahydroxybenzene,
hexahydroxybenzene,
1,2,3-benzenetricarboxylic acid,
1,2,4-benzenetricarboxylic acid,
1,3,5-benzenetricarboxylic acid,
3,4,5-trihydroxybenzoic acid,
methyl 3,4,5-trihydroxybenzoate,
1,2,3-trihydroxytoluene,
2,4,5-trihydroxytoluene,
2,4,6-trihydroxytoluene,
3,4,5-trihydroxytoluene,
pyromellitic anhydride,
1,2,3,4-tetrahydroxynaphthalene,
2,3,4-trihydroxyanthracene,
1,2,3-trihydroxy-9,10-anthraquinone and
1,2,4-trihydroxy-9,10-anthraquinone.

$Z^2$ is furthermore a polycyclic radical $Z^2/2$ of the formula

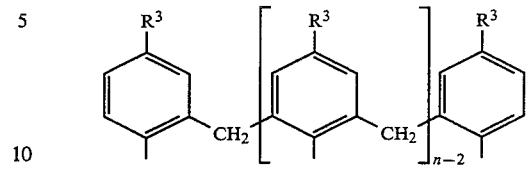

where $R^3$ may be $C_1$- to $C_4$-alkyl, $C_1$- to $C_4$-alkoxy or halogen.

In the case where n=3, the central unit $Z^2/3$ may be a phosphorus-containing radical

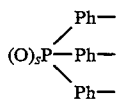

where s may be zero or 1.
Preferred compounds are
1,3,5-trihydroxybenzene,
pyromellitic anhydride and
methyl 3,4,5-trihydroxybenzoate, and
the radical

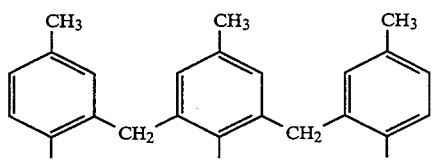

$X^2$ is essentially a hetero unit oxygen, sulfur, —CO—O—, —O—CO—, —SO$_2$—, —SO$_2$—O—, —O—SO$_2$—O—, —NR$^4$—, —CO—NR$^4$—, —NR$^4$—O— or —CO—N<,
where $R^4$ may be hydrogen or $C_1$- to $C_8$- alkyl, with the proviso that, in the case of a polycyclic radical $Z^2/2$, $X^2$ can only be —O— —O—CO—.

Preference is given to oxygen, —CO—O— and —O—CO—.

$R^1$ is a $C_2$- to $C_{20}$-bridge having 2 to 12 bridging members which may be interrupted by oxygen, sulfur or —NR$^4$—, it being possible for each of these hetero units to be separated by at least 2 carbon atoms.

Examples of highly suitable bridging members $R^1$ are —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_{10}$—, —(CH$_2$)$_{12}$—, —(CH$_2$—O—CH$_2$)$_2$—,

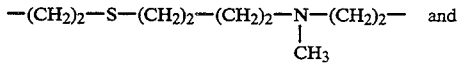

—CH—CH$_2$—.
  |
  CH$_3$

Particularly highly suitable bridging members $R^1$ are —(CH$_2$)$_5$—, —(CH$_2$)$_6$—, —(CH$_2$)$_7$— and —(CH$_2$)$_{10}$—.

Y is a chemical bond, oxygen, sulfur, —CO—O—, —O—CO—, —NR$^4$—, —CO—NR$^4$— or —NR$^4$—CO—, where $R^4$ may be hydrogen or $C_1$- to $C_8$-alkyl.

Oxygen is particularly preferred.

Highly suitable mesogenic groups M are groups of the formula III

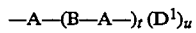   III where
- A is 1,4-phenylene or 2,6-naphthylene, which may contain up to two nitrogen atoms as hetero atoms and may carry up to two fluorine, chlorine, bromine, nitro or cyano substituents, or is 1,4-cyclohexylene, which may contain up to two hetero atoms from oxygen, sulfur and nitrogen, in each case in non-adjacent positions,
- B is a chemical bond or one of the following bridging members:
  —CO—O—, —O—CO—, —CH$_2$—CH$_2$—, —CH$_2$—O—, —O—CH$_2$—, —CH$_2$—S—, —S—CH$_2$—, —C≡C—, —CH=CH—, —CH=N—, —N=CH—, —N=N—,

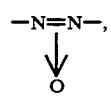

—CH=CH—CO—O— and —O—CO—CH=CH—,

- D$^1$ is a fluorine, chlorine, bromine, nitro, cyano, —OCFH$_2$, —OCF$_2$H, —OCF$_3$, —O—CO—R$^5$ or —CO—O—R$^5$ substituent, where R$^5$ is linear C$_1$- to C$_{20}$-alkyl, which may be interrupted by oxygen and may be asymmetrically substituted by fluorine, chlorine, bromine, cyano or methyl,
- t is a number from 1 to 4, with the proviso that A and B may be different from one another, and
- u is 1 if D$^1$ is linked to an aromatic ring and 1 or 2 if D$^1$ is linked to a cyclohexylene ring.

A preferred mesogenic group M is

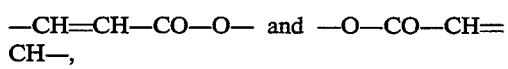

Other highly suitable mesogenic groups M are groups of the formula IV

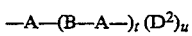   IV where D$^2$ is one of the following enantiomeric groups: linear C$_1$- to C$_{20}$-alkyl which is asymmetrically substituted on one or two carbon atoms by fluorine, chlorine, bromine, cyano, trifluoromethyl or methyl and may be interrupted once by —CO—O— or up to twice by —O—, or linear C$_3$- to C$_6$-alkyl which is interrupted by

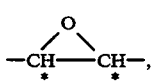

with the proviso that these enantiomeric groups D$^2$ may be linked to A via —O—, —CO—O— or —O—CO—.

Examples of highly suitable enantiomeric groups D$^2$ are:

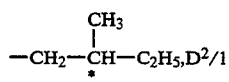 D$^2$/1

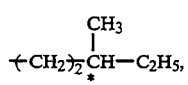 D$^2$/2

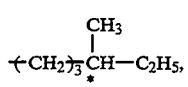 D$^2$/3

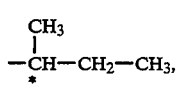 D$^2$/4

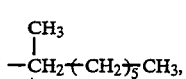 D$^2$/5

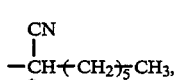 D$^2$/6

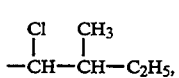 D$^2$/7

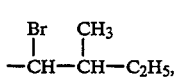 D$^2$/8

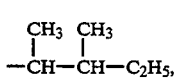 D$^2$/9

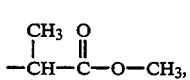 D$^2$/10

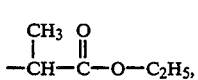 D$^2$/11

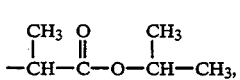 D$^2$/12

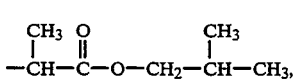 D$^2$/13

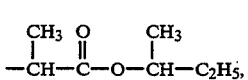 D$^2$/14

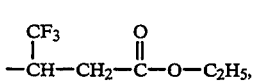 D$^2$/15

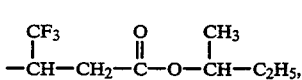 D$^2$/16

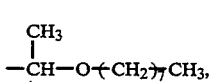 D$^2$/17

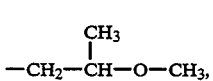 D$^2$/18

-continued

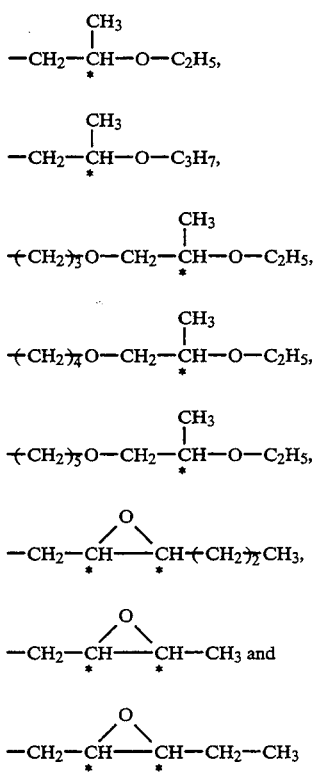

of which D²/6, D²/7, D²/11, D²/15, D²/17 to D²/21 and D²/24 are particularly suitable.

A preferred mesogenic group is

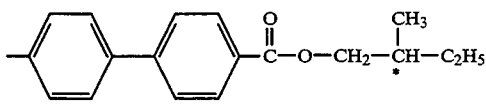

For the preparation of the liquid-crystalline compounds I, the general principle is to react alcohols $Z^1(H)_m$ with carboxylic acid halides M—Y—R¹—CO—Hal where Hal is chlorine or bromine, or carboxylic acids $Z(H)_m$ or derivatives thereof, such as acid chlorides $Z^1(Cl)_m$ or anhydrides $(Z^1)_2O$ with alcohols M—Y—R¹—OH.

In detail, the liquid-crystalline compounds I are obtainable by the following methods:

A carboxylic acid M—Y—R¹—COOH is reacted in a known manner with thionyl chloride in the presence of dimethylformamide to give the carboxylic acid chloride M—Y—R¹—CO—Cl. In the next step, reaction of the acid chloride M—Y—R¹—CO—Cl with an alcohol $Z^1(H)_m$ in the presence of pyridine gives the compound I.

Alcoholysis of carboxylic acid chlorides is known in general terms in numerous variants, so that further details in this respect are superfluous. It should merely be added that it is usually advisable to employ the acid chloride in excess in order to react the alcohol quantitatively. After the product I has been isolated, additional purification by means of gel chromatography and subsequent recrystallization can be carried out, for which purpose methylene chloride and/or methanol mixtures are usually suitable.

A further way of preparing the liquid-crystalline compound I is acid-catalyzed esterification of carboxylic acids $Z^1(H)_m$, acid chlorides $Z^1(Cl)_m$ and anhydrides $(Z^1)_2O$ using alcohols M—Y—R¹—OH.

Esterification is known in general terms in numerous variants with respect to the acid, temperature and reaction time.

One variant for the reaction of $Z^1(H)_m$ with carboxylic acid chlorides is the reaction with ω-bromocarboxylic acid chlorides Br—R¹—CO—Cl and subsequent etherification of the intermediate $Z^1$—CO—R¹—Br using an alcoholic compound HO-M to give the compound I.

The general principle for the preparation of the liquid-crystalline compounds II is to react phenolic compounds $Z^2(OH)_n$ with compounds derived from compounds of the M—Y—R¹—X²—H type or derivatives thereof, or with an alkyl bromide M—Y—R¹—Br.

The compounds II are furthermore obtained in a known manner by reacting the compound $Z^2(OH)_n$ with an ω-bromocarboxylic acid chloride Br—R¹—CO—Cl via an intermediate $Z^2$(—O—CO—R¹—Br)$_n$, which is subsequently etherified using the compound HO-M.

Another way of preparing the compounds II is to esterify carboxylic acids $Z^2(COOH)_n$, acid chlorides $Z^2(COCl)_n$ or anhydrides $(Z^2CO)_2$ using compounds of the M—Y—R¹—OH type; this reaction is carried out in a conventional manner.

The liquid-crystalline compounds I and II according to the invention can be prepared in high purity in a uniform molecular weight, have fast response times and have high dielectric anisotropy. In addition, they have virtually no tendency toward crystallization.

The liquid-crystalline compounds I and II according to the invention alone, in mixtures with one another and with other liquid-crystalline and/or non-liquid-crystalline compounds, are highly suitable in the form of solid or liquid-crystalline, optically anisotropic media for the display and storage of information. In addition, they are suitable for the preparation of anisotropic, solid, optical media for optical components, such as compensators, polarizers, prisms, plates having optical rotation and electro-optical storage displays.

EXAMPLES

The phase transitions were determined under a polarizing microscope (Leitz, Ortholux II Pol BK, Mettler FP 82 HT heating stage, Mettler FP 80 control unit), heating rate 10° C./min, and by DSC measurements (Perkin-Elmer, DSC-7), heating rate 20° C./min.

The following symbols denote the phases. A phase change takes place at the phase-transition temperatures measured.

c = crystalline
g = glass state
n = nematic
ch = cholesteric
s = smectic
i = isotropic The transition temperatures (°C.) of the compounds according to the invention are indicated in each of the examples. The temperatures in parentheses denote monotropic phase transitions. These are taken to mean phase transitions which only proceed in one direction, for example if the liquid-crystalline state can only be achieved by supercooling the melt. The melting point is then higher than the clearing point.

Preparation of the liquid-crystalline compounds I.

EXAMPLE 1

Pentaerythritol tetra(ω-(4'-cyanobiphenyl-4-oxy)pentylcarboxylate)

a) 6-(4'-cyanobiphenyl-4-oxy)caproic acid

A mixture comprising 41.3 g (212 mmol) of 4-(4'-hydroxybiphenyl)carbonitrile, 49.5 g (254 mmol) of 6-bromocaproic acid, 42.1 g (254 mmol) of potassium iodide, 70.1 g (508 mmol) of potassium carbonate and 400 ml of 2-butanone was refluxed for 32 hours. The residue produced on cooling was separated off, washed with 2-butanone, taken up in dilute hydrochloric acid, stirred for a few minutes, isolated and washed with water. Finally, the product was recrystallized twice from toluene.

Yield: 30% Melting point: 168° C.

b) 6-(4'-Cyanobiphenyl-4-oxy)caproyl chloride

A solution comprising 16.3 g (52.7 mmol) of 6-(4'-cyanobiphenyl-4-oxy)caproic acid, 7.5 g (63.3 mmol) of thionyl chloride and 3 drops of dimethylformamide in 160 ml of toluene was heated at the boil for 1.5 hours. The readily volatile constituents were removed under reduced pressure at 80° C. and the residue was dried under reduced pressure at room temperature.

Yield: 90% c) Pentaerythritol tetra(ω-(4'-cyanobiphenyl-4-oxy)pentylcarboxylate)

10.9 g (33.3 mmol) of 6-(4'-cyanobiphenyl-4-oxy)caproyl chloride were added to a solution comprising 0.9 g (6.7 mmol) of pentaerythritol, 3.2 g (40 mmol) of pyridine and 90 ml of methylene chloride, and the mixture was then stirred overnight at room temperature with exclusion of moisture. Work-up gave 8.3 g of crude product, which was purified by chromatography on silica gel (eluent: toluene/ethyl acetate=3/1) and recrystallization from methylene chloride/methanol.

Yield: 40% $^1$H-NMR (CDCl$_3$, TMS): δ (ppm): 1.4–1.9 (m,24H,CH$_2$); 2.37 (t,8H,CH$_2$); 4.0 (t,8H,CH$_2$); 4.2 (s,8H,CH$_2$); 6.95 (d,8H,arom.-H); 7.5 (d,8H,arom.-H); 7.55–7.8 (m,16H,arom.-H)

Phase transitions: g-n 25° C. n-i 90° C.

EXAMPLE 2

Pentaerythritol tetra(ω-(4'-cyanobiphenyl-4-oxy)heptylcarboxylate)

a) 8-(4'-Cyanobiphenyl-4-oxy)octanoic acid

The preparation was carried out as in Example 1a), but the 6-bromocaproic acid was replaced by 8-bromooctanoic acid.

Yield: 30% Melting point: 147°–148° C.

b) 8-(4'-Cyanobiphenyl-4-oxy)octanoyl chloride

The preparation was carried out as in Example 1b), but the 6-(4'-cyanobiphenyl-4-oxy)caproic acid was replaced by 8-(4'-cyanobiphenyl-4-oxy)octanoic acid.

Yield: 95% Melting point: 57°–58° C.

c) Pentaerythritol tetra(ω-(4'-cyanobiphenyl-4-oxy)heptylcarboxylate

The preparation was carried out as in Example 1c), but the 6-(4'-cyanobiphenyl-4-oxy)caproyl chloride was replaced by 8-(4'-cyanobiphenyl-4-oxy)octanoyl chloride.

Yield: 38% $^1$H NMR (CDCl$_3$, TMS): δ (ppm): 1.1–1.93 (m40H,CH$_2$); 2.3 (t,8H,CH$_2$); 4.0 (t,8H,CH$_2$); 4.12 (s,8H,CH$_2$); 7.0 (d,8H,arom.-H); 7.53 (d,8H,arom.-H); 7.6–7.8 (m,16H,arom.-H)

Phase transitions: g-s 20° C. s-n 80° C. n-i 95° C.

EXAMPLE 3

Mannitol hexa(ω-(4'-cyanobiphenyl-4-oxy)pentylcarboxylate)

The preparation was carried out as in Examples 1a), 1b) and 1c), but the pentaerythritol was replaced by mannitol.

Yield: 35% $^1$H-NMR (CDCl$_3$, TMS): δ (ppm): 1.38–1.9 (m,36H,CH$_2$); 2.27–2.52 (m,12H,CH$_2$); 3.88–4.1 (m,14H,CH$_2$); 4.2–4.38 (m,2H,CH$_2$); 5.0–5.2 (m,2H,CH); 5.43–5.55 (m,2H,CH); 6.9–7.07 (m,12H,arom.-H); 7.4–7.75 (m,36H,arom.-H)

Phase transitions: g-ch 34° C. ch-i 115° C.

EXAMPLE 4

Mannitol hexa(ω-(4'-cyanobiphenyl-4-oxy)heptylcarboxylate)

The preparation was carried out as in Examples 2a), 2b) and 2c), but the pentaerythritol was replaced by mannitol.

Yield: 36% $^1$H-NMR (DMSO-d$_6$, TMS): δ (ppm): 1.0–1.8 (m,60H,CH$_2$); 2.1–2.4 (m,12H,CH$_2$); 3.7–4.1 (m,14H,CH$_2$); 4.2–4.32 (m,2H,CH$_2$); 4.9–5.1 (m,2H,CH); 5.35–5.5 (m,2H,CH); 6.8–7.1 (m,12H,arom.-H); 7.5–8.0 (m,36H,arom.-H)

Phase transitions: g-s 27° C. s-ch 116° C. ch-i 117° C.

EXAMPLE 5

Bis[1,2,3-tri[4-(S-2-methylbutoxycarbonyl)biphenyl-4'-yl-oxyundecyloxycarbonyl]-2-propyl adipate a) S-2-methylbutyl 4-(4'-ω-hydroxyundecyloxy)biphenylcarboxylate 36.1 g (127 mmol) of S-2-methylbutyl 4-(4'-hydroxybiphenyl)carboxylate, 32 g (127 mmol) of 11-bromo-1-undecanol and 20 g (145 mmol) of anhydrous potassium carbonate were stirred in 500 ml of dimethylformamide at 100° C. until the hydroxybiphenylcarboxylate had reacted completely; this was determined by thin-layer chromatography. The mixture was cooled to room temperature, and the solid byproduct was separated off and discarded. The solvent was removed from the filtrate, and the solid crude product was recrystallized twice from acetone.

Yield: 45% b) Tri[4-(S-2-methylbutoxycarbonyl)biphenyl-4'-yl-oxyundecyl] 2-hydroxy propane-1,2,3 tricarboxylate 0.8 g (3.6 mmol) of citric acid, 5 g (11 mmol) of S-2-methylbutyl 4-(4'-ω-hydroxyundecyloxy)biphenylcarboxylate and 1 g of p-toluenesulfonic acid were refluxed in 150 ml of anhydrous toluene. The vapor phase was condensed, the water present therein was removed, and the toluene phase was recycled. When the reaction was complete, the solvent and p-toluenesulfonic acid were removed and the residue was purified by chromatography on silica gel (eluent: toluene/ethyl acetate=5/1) and recrystallization from methanol.

Yield: 30% c) Bis[1,2,3-tri[4-(S-2-methylbutoxycarbonyl)biphenyl4'-yloxyundecyloxycarbonyl]-2-propyl adipate 3.5 g (2.3 mmol) of tri[4-(S-2-methylbutoxycarbonyl)-biphenyl- 4'-yloxyundecyl] 2-hydroxy propane-1,2,3 tricarboxylate, 0.3 ml of triethylamine and 50 mg of 4-dimethylaminopyridine were treated in 100 ml of methylene chloride at a temperature of from −5° to −10° C. with 0.27 ml (1.2 mmol) of adipoyl dichloride, and the mixture was stirred at this temperature for 30 minutes, warmed to room temperature and stirred until the citric acid derivative had reacted completely. Water was then added to the reaction mixture, the organic phase was separated off and dried using anhydrous sodium sulfate, and the solvent was removed. The residue was dissolved in tetrahydrofuran and precipitated using petroleum ether.

Yield: 82% $^1$H-NMR (CDCl$_3$, TMS): δ (ppm): 0.95–1.95 (m,CH,CH$_2$,CH$_3$,); 2.75–2.95 (m,CH$_2$); 3.95–4.30 (m,OCH$_2$); 6.90–8.10 (m,arom.-H)

EXAMPLE 6

Glycerol tri(ω-(4'-cyanobiphenyl-4-oxy)heptylcarboxylate)

a) Glycerol tri(ω-bromoheptylcarboxylate)

80 g (330 mmol) of 8-bromooctanoyl chloride, dissolved in 80 ml of methylene chloride, were added to a solution comprising 9 g (100 mmol) of glycerol, 26 g (330 mmol) of pyridine and 300 ml of methylene chloride, and the mixture was then stirred for 24 hours at room temperature with exclusion of moisture. Work-up gave 68 g of product. Yield: 96% b) Glycerol tri(ω-(4'-cyanobiphenyl-4-oxy)heptylcarboxylate)

7.1 g (10 mmol) of glycerol tri(ω-bromoheptylcarboxylate), 6.2 g (32 mmol) of 4-(4'-hydroxybiphenyl)-carbonitrile, 4.4 g (32 mmol) of freshly ground and ignited potassium carbonate and 0.5 g of potassium iodide were refluxed for 48 hours in 70 ml of 2-butanone. The solution was then introduced into water, the organic phase was extracted with ethyl acetate, and the product was worked up. 8 g of crude product were obtained, which were purified by chromatography on silica gel (eluent: toluene/ethyl acetate=1/1).

Yield: 17% $^1$H-NMR (CDCl$_3$, TMS): δ (ppm): 1.21–1.35 (m,18H,CH$_2$); 1.55–1.7 (m,6H,CH$_2$); 1.7–1.9 (m,6H,CH$_2$); 2.33(t,6H,CH$_2$); 3.97 (t,6H,CH$_2$); 4.1–4.25 (m,2H,CH$_2$); 4.25–4.4 (m,2H,CH$_2$); 5.3 (m,1H,CH); 6.93 (d,6H,arom.-H); 7.5 (d,6H,arom.-H); 7.57–7.8 (m,12H,arom.-H)

Phase transitions: g-n 13° C. n-i 91° C.

EXAMPLE 7

Glycerol tri(ω-(4'-cyanobiphenyl-4-oxy)decylcarboxylate)

a) Glycerol tri(ω-bromodecylcarboxylate)

The preparation was carried out as in Example 6a), but the 8-bromooctanoyl chloride was replaced by 11-bromoundecanoyl chloride.

b) Glycerol tri(ω-(4'-cyanobiphenyl-4-oxy)decylcarboxylate)

The preparation was carried out as in Example 6b), but the glycerol tri(ω-bromoheptylcarboxylate) was replaced by glycerol tri(ω-bromodecylcarboxylate).

Yield: 15% $^1$H-NMR (CDCl$_3$, TMS): δ (ppm): 1.2–1.4 (m,30H,CH$_2$); 1.4–1.5 (m,6H,CH$_2$); 1.5–1.7 (m,6H,CH$_2$); 1.7–1.9 (m,6H,CH$_2$); 2.3 (t,6H,CH$_2$); 4.0(t,6H,CH$_2$); 4.1–4.2 (m,2H,CH$_2$); 4.26–4.35 (m,2H,CH$_2$); 5.28 (m,1H,CH); 6.95 (d,6H,arom.-H); 7.53 (d,6H,arom.-H); 7.55–7.8 (m,12H,arom.-H)

Phase transitions: g-s 8° C. s-n 84° C. n-i 90° C.

Preparation of the liquid-crystalline compounds II

EXAMPLE 8

Methyl 3,4,5-tri(4-(4'-hexyloxy)biphenylcarbonitriloxy)benzoate 1.8 g (10 mmol) of methyl 3,4,5-trihydroxybenzoate, 10.7 g (30 mmol) of 4-(4'-ω-bromohexyloxy)biphenylcarbonitrile, 4.1 g (30 mmol) of freshly ground and ignited potassium carbonate, 5 g (30 mmol) of potassium iodide and 50 ml of anhydrous nitrobenzene were heated at 150° C. for 8 hours with stirring. The mixture was cooled to room temperature, and the suspension was filtered, nitrobenzene was removed from the filtrate by distillation, and the residue was purified by chromatography on silica gel (eluent:toluene/ethyl acetate=2/1). The main fraction was subsequently dissolved in 30 ml of methylene chloride, and the solution was added dropwise with stirring to 200 ml of cold methanol. The precipitated product was filtered off, washed with cold methanol and dried.

Yield: 39% $^1$H-NMR (CDCl$_3$, TMS); δ (ppm): 1.4–1.5 (m,12H,CH$_2$); 1.5–2.1 (m,12H,CH$_2$); 3.92 (s,3H,OCH$_3$); 3.8–4.2 (m,12H,CH$_2$-O); 6.8–7.1 (m,6H,arom.-H); 7.28 (s,2H,arom.-H); 7.3–7.8 (m,18H,arom.-H)

Phase transitions: c-g 127° C. g-n (27° C.) n-i (125 ° C.)

EXAMPLE 9

1,3,5-tri(4-(4'-hexyloxy)biphenylcarbonitriloxy)benzene

The preparation was carried out as in Example 8, but the methyl 3,4,5-trihydroxybenzoate was replaced by 1,3,5-trihydroxybenzene.

Yield: 35% $^1$H-NMR (CDCl$_3$, TMS); δ (ppm): 1.36–1.7 (m,12H,CH$_2$); 1.7–2.1 (m,12H,CH$_2$); 3.93 (t,6H,CH$_2$-O); 4.02 (t,6H,CH$_2$-O); 6.09 (s,3H,arom.-H); 7.0 (d,6H,arom.-H); 7.4–7.8 (m,18H,arom.-H)

Phase transitions: g-n 25° C. n-i 116° C.

EXAMPLE 10

Phloroglucine tri(ω-(4'-cyanobiphenyl-4-oxy)heptylcarboxylate)

The preparation was carried out as in Example 2c), but, instead of pentaerythritol, 1,3,5-trihydroxybenzene was reacted with 8-(4'-cyanobiphenyl-4-oxy)octanoyl chloride.

Yield: 35% $^1$H-NMR (DMSO-d$_6$, TMS): δ (ppm): 1.1–1.55 (m,18H,CH$_2$); 1.55–1.9 (m,12H,CH$_2$); 2.52 (t,6H,CH$_2$); 4.0 (t,6H,CH$_2$); 6.9 (s,3H,arom.-H); 7.03 (d,6H,arom.-H); 7.66 (d,6H,arom.-H); 7.72–8.0 (m,12H,arom.-H)

Phase transitions: c-g 114° C. g-n 22° C. n-i 98° C.

EXAMPLE 11

Tetra (4-(4'-hexyloxy)biphenylcarbonitrilyl) 1,2,4,5-benzenetetracarboxylate 1.1 g (5 mmol) of pyromellitic anhydride, 5.2 g (20 mmol) of 4-(4'-ω-hydroxyhexyloxy)biphenylcarbonitrile, 0.2 g of p-toluenesulfonic acid and 50 ml of xylene were refluxed for 12 hours on a water separator. The mixture was cooled, and 100 ml of methylene chloride were added. The residue remaining after work-up was purified by chromatography on silica gel ( eluent:toluene/ethyl acetate=4/1), and the main fraction was purified by recrystallization from toluene.

Yield: 32% $^1$H-NMR (DMSO-d$_6$, TMS): δ (ppm): 1.3–1.52 (m,16H,CH$_2$); 1.6–1.8 (m,16H,CH$_2$); 3.97 (t,8H,CH$_2$); 4.3 (t,8H,CH$_2$); 7.0 (d,8H,arom.-H); 7.65 (d,8H,arom.-H); 7.72–7.9 (m,16H,arom.-H); 8.1 (s,2H,arom.-H);

Phase transitions: c-n 140° C. n-i (98° C.)

EXAMPLE 12

Determination of the response times

The fastest response times τ of three liquid-crystalline compounds (Examples 7, 8 and 9) and of a polymeric liquid crystal built up from the monomer unit

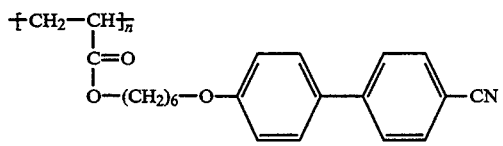

were determined.

Each of the measurements was carried out using a 2 µm cell with a rubbed polyimide layer from EHC Co. Ltd. The switching experiments were all carried out using a rectangular voltage of ±15V and 1 kHz.

TABLE

| Liquid crystal | Clearing point (°C.) | Switching range (°C.) | Fastest response time (ms) |
|---|---|---|---|
| Example 7 | 90.0 | 78–89.5 | 1.98 (89.5° C.) |
| Example 8 | 125.7 | 54–125.5 | 0.70 (125.5° C.) |
| Example 9 | 117.5 | 65–116.0 | 2.24 (116° C.) |
| Polymer | 124.5 | 116–124.0 | 20.20 (145° C.) |

We claim:

1. A liquid-crystalline compound of the formula I or II

where $Z^1$ is the alcoholate or acid radical $Z^1/1$ of an m-valent aliphatic alcohol or of an m-valent aliphatic carboxylic acid having 3 to 30 carbon atoms, where m is other than 4, the alcoholate or acid radical $Z^1/2$ of an m-valent cycloaliphatic alcohol or of an m-valent cycloalphatic carboxylic acid having 5 or 6 ring members; in the case where m=3, the nitrogen-containing radical $Z^1/3$

where p may be 1 or 2, in the case where m=3, a radical having the structure $Z^1/4a$–d

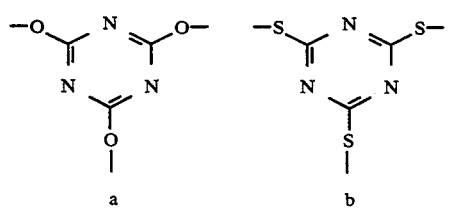

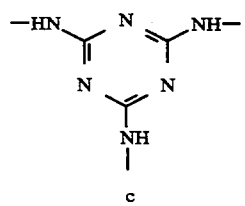

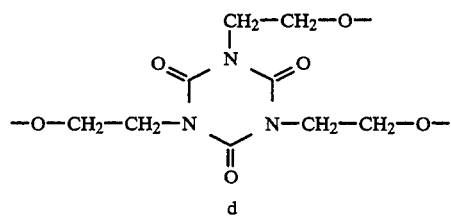

in the case where m=3, or m=4, the acid radical $Z^1/5$ of nitrilotriacetic acid or ethylenediaminetetraacetic acid, the radical $Z^1/6$

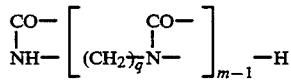

where q may be 2 or 3, is the n-valent radical $Z^2/1$ of a benzene

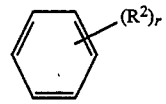

where $R^2$ may be halogen, cyano, nitro, $C_1$–$C_{10}$-alkyl, $C_1$ to $C_{10}$-alkoxy, $C_1$- to $C_{10}$-alkoxycarbonyl, $C_1$- to $C_{10}$-acyloxy or radicals which are bonded to the ring in the vicinal position, r is zero to 3, and the radicals $R^2$, in the case where r>1, may be identical or different, the polycyclic radical $Z^2/2$

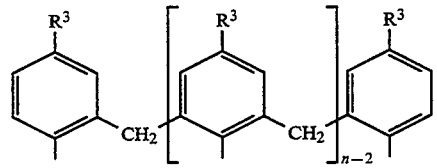

where $R^3$ may be $C_1$- to $C_4$-alkyl, $C_1$- to $C_4$-alkoxy or halogen, in the case where n=3, the phosphorus-containing radical $Z^2/3$

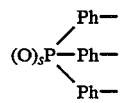

where s may be zero or 1;

$X^1$ is a chemical bond or —CO—, $X^2$ is oxygen, sulfur, —CO—O—, —O—CO—, —SO$_2$, SO$_2$—O—, —O—SO$_2$—O—, —NR$^4$—, —CO—NR$^4$—, —NR$^4$—O— or —CO—N<, where $R^4$ may be hydrogen or $C_1$- to $C_8$-alkyl, with the proviso that, in the case of the polycyclic radical $Z^2/2$, $X^2$ can only be —O— or —O—CO—, m is 3 to 6, with the proviso that m is less than or equal to the number of carbon atoms in $Z^1$ or $Z^2$, n is 3 to 6, $R^1$ is a $C_2$- to $C_{20}$- bridge containing 2 to 12 bridging members, which may be interrupted by oxygen, sulfur or —NR$^4$—, it being possible for each of these hetero units to be separated by at least 2 carbon atoms, Y is a chemical bond, oxygen, sulfur, —CO—O—, —O—CO—, —NR⁴—, —CO—NR⁴— or —NR⁴—CO—, and M is a mesogenic group of the formula III or IV

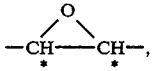   III

—A—(B—A—)ᵣ—(D²)ᵤ   IV where
- A is a 1,4-phenylene or 2,6-naphthylene, which may contain up to two nitrogen atoms as hetero atoms and may carry up to two fluorine, chlorine, bromine, nitro or cyano substituents, or is 1,4-cyclohexylene, which may contain up to two hetero atoms from oxygen, sulfur and nitrogen, in each case in non-adjacent positions,
- B is a chemical bond or one of the following bridging members:
  —CO—O—, —O—CO—, —CH₂—CH₂—, —CH₂—O—, —O—CH₂—, —CH₂—S—, —S—CH₂—, —C≡C—, —CH=CH—, —CH=N—, —N=CH—, —N=N—,

—N=N—
    ↓
    O

—CH=CH—CO—O— and —O—CO—CH=CH—,
- D¹ is a fluorine, chlorine, bromine, nitro, cyano, —OCFH₂, —OCF₂H, —OCF₃, —O—CO—R⁵ or —CO—O—R⁵ or substituent, where R⁵ is linear C₁- to C₂₀-alkyl, which may be interrupted by oxygen and may be asymmetrically substituted by fluorine, chlorine, bromine, cyano or methyl,
- D² is one of the following enantiomeric groups: linear C₁- to C₂₀-alkyl which is asymmetrically substituted on one or two carbon atoms by fluorine, chlorine, bromine, cyano, trifluoromethyl or methyl and may be interrupted once by —CO—O— or up to twice by —O—, or linear C₃- to C₆-alkyl which is interrupted by

with the proviso that these enantiomeric groups D² may be linked to A via —O—, —CO—O— or —O—CO—,
- t is a number from 1 to 4, with the proviso that A and B may be different from one another, and
- u is 1 if D¹ or D² is linked to an aromatic ring and 1 or 2 if D¹ or D² is linked to a cyclohexylene ring.

2. The compound of claim 1 wherein the compound is selected from the group consisting of
- mannitol hexa(ω-(4'cyanobiphenyl-4-oxy)pentylcarboxylate),
- mannitol hexa(ω-(4'cyanobiphenyl-4-oxy)heptylcarboxylate),
- bis[1,2,3-tri[4-(S-2-methylbutoxycarbonyl)biphenyl-4'-yl-oxyundecyloxycarbonyl]-2-propyl adipate,
- glycerol tri(ω-(4'cyanobiphenyl-4-oxy)heptylcarboxylate),
- glycerol tri(ω-(4'cyanobiphenyl-4-oxy)decylcarboxylate),
- methyl 3,4,5-tri(4-(4'hexyloxy)biphenylcarbonitriloxy)benzoate,
- 1,3,5-tri(4-(4'-hexyloxy)biphenylcarbonitriloxy)-benzene,
- phloroglucine tri(ω-(4'-cyanobiphenyl-4oxy)heptylcarboxylate), and
- tetra(4-(4'-hexyloxy)biphenylcarbonitrilyl)1,2,4,5-benzentetracarboxylate.

3. The compound of claim 1 wherein M is of the formula III.

4. The compound of claim 1 wherein M is of the formula IV.

* * * * *

UNITED STATES PATENT AND TRADEMARK OFFICE
CERTIFICATE OF CORRECTION

PATENT NO. : 5,417,882

DATED : May 23, 1995

INVENTOR(S) : BACH et al.

It is certified that error appears in the above-indentified patent and that said Letters Patent is hereby corrected as shown below:

On the title page:

item [57], line 8 after the formulas, delete "-CO-$NR^4$-$NR^4$-O" and replace with -- -CO-$NR^4$- -$NR^4$-O- --.

Column 19, claim 1, line 34, delete "or".

Signed and Sealed this

Eighth Day of August, 1995

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO.: 5,417,882

DATED: May 23, 1995

INVENTOR(S): BACH et al.

It is certified that error appears in the above-identified patent and that said Letters Patent is hereby corrected as shown below:

Column 9, line 19, "-C=C-" should be -- -C≡C- --.

Signed and Sealed this

Twenty-eighth Day of November 1995

Attest:

BRUCE LEHMAN

Attesting Officer      Commissioner of Patents and Trademarks